US008754064B2

(12) United States Patent
M'Rabet et al.

(10) Patent No.: US 8,754,064 B2
(45) Date of Patent: Jun. 17, 2014

(54) MILK OLIGOSACCHARIDE FOR STIMULATING THE IMMUNE SYSTEM

(75) Inventors: Laura M'Rabet, Soesterberg (NL); Antonie Van Baalen, Arnhem (NL); Bernd Stahl, Rosbach-Rodheim (DE); Arjan Paul Vos, Bennekom (NL); Thomas Hubertus Martinus Snoeren, Steenwijk (NL)

(73) Assignee: N.V. Nutricia, Zoetermeer (NL)

( * ) Notice: Subject to any disclaimer, the term of this patent is extended or adjusted under 35 U.S.C. 154(b) by 839 days.

(21) Appl. No.: 12/294,768

(22) PCT Filed: Mar. 21, 2007

(86) PCT No.: PCT/NL2007/050119
§ 371 (c)(1),
(2), (4) Date: Apr. 30, 2009

(87) PCT Pub. No.: WO2007/114696
PCT Pub. Date: Oct. 11, 2007

(65) Prior Publication Data
US 2010/0035828 A1 Feb. 11, 2010

(30) Foreign Application Priority Data

Mar. 30, 2006 (NL) .............. PCT/NL2006/050065

(51) Int. Cl.
C07H 3/00 (2006.01)
A61K 31/702 (2006.01)
(52) U.S. Cl.
CPC ............... C07H 3/00 (2013.01); A61K 31/702 (2013.01)
USPC ........................................ 514/61; 536/18.7
(58) Field of Classification Search
None
See application file for complete search history.

(56) References Cited

U.S. PATENT DOCUMENTS

| 5,635,606 A | * | 6/1997 | Heerze et al. ............... 530/412 |
| 7,939,118 B2 | | 5/2011 | Stahl et al. |
| 2004/0072794 A1 | * | 4/2004 | Kaup et al. ..................... 514/54 |

FOREIGN PATENT DOCUMENTS

| EP | 1 242 436 B1 | 9/2002 |
| EP | 1 634 599 A1 | 3/2006 |
| WO | WO-92/11017 A2 | 7/1992 |
| WO | WO-99/08511 A1 | 2/1999 |
| WO | WO 01/42263 A2 | 6/2001 |
| WO | WO 2005/039597 A2 | 5/2005 |
| WO | WO 2005/067962 A2 | 7/2005 |
| WO | WO 2006/019300 A2 | 2/2006 |

OTHER PUBLICATIONS

International Search Report PCT/NL2007/050119 dated Jun. 26, 2007.
Antonio Martinez-Ferez et al., "Goats' milk as a natural source of lactose-derived oligosaccharides: Isolation by membrane technology", International Dairy Journal 16 (2006) 173-181.
Taku Nakano et al., "Sialic Acid in Human Milk: Composition and Functions", Acta Paediatr Tw, vol. 42, No. 1, 2001, pp. 11-17.
E. Riva et al., "Closer to the Gold Standard: an Appraisal of Formulae Available in Italy for Use in Formula-fed Infants", The Journal of International Medical Research, 2005; 33:595-611.
Tadashi Nakamura et al., "Sialyllactose occurs as free lactones in ovine colostrum", Biochimica et Biophysica Acta 1381 (1998) 286-292.
Wendy H. Oddy M.P.H., Ph.D. "A Review of the Effects of Breastfeeding on Respiratory Infections, Atopy and Childhood Asthma", Journal of Asthma, vol. 41, No. 6, pp. 605-621, 2004.
C. Kunz et al., "Oligosaccharides in Human Milk: Structural, Functional, and Metabolic Aspects", Annu. Rev. Nutr. 2000, 20:699-722.
International Search Report for PCT/NL2006/050065, dated Dec. 12, 2006, 3 pages.

* cited by examiner

Primary Examiner — Eric S Olson
(74) Attorney, Agent, or Firm — Gilberto M. Villacorta; Sunit Talapatra; Foley & Lardner LLP

(57) ABSTRACT

The present invention relates to methods and nutritional compositions for stimulating the immune system, particularly in subjects with an impaired immune system such as 5 infants, said method comprising administering a composition comprising sheep milk and/or short chain oligosaccharides.

13 Claims, No Drawings

MILK OLIGOSACCHARIDE FOR STIMULATING THE IMMUNE SYSTEM

FIELD OF THE INVENTION

The present invention relates to methods and nutritional compositions for stimulating the immune system, particularly in subjects with an impaired immune system such as infants.

BACKGROUND OF THE INVENTION

A functioning immune system is important for health. Subjects having an impaired immune system due to for example sickness, or subjects wherein the immune system is under development (e.g. infants) can greatly benefit of compositions capable of stimulating the immune system.

WO2005039597 describes a method for enhancing the immune system and the treatment and/or prevention of immune system related disorders in a mammal, particularly newborns, which method comprises the administration of acid oligosaccharide and neutral oligosaccharide.

EP1242436 describes an oligosaccharide mixture based on oligosaccharides produced from one or several animal milks and which are composed of two or more monosaccharide units, wherein the proportion of neutral oligosaccharides to acidic oligosaccharides is 90-60. The oligosaccharide mixture described approximates human milk with respect to its positive properties and in particular its anti-infective activity.

SUMMARY OF THE INVENTION

It was surprisingly found that oligosaccharides isolated from sheep milk strongly stimulate the immune system, and therefore can advantageously be used to treat and/or prevent immune system related disorders. Stimulation of the immune system is particularly useful in subjects where the immune system is impaired or underdeveloped, particularly infants, elderly and hospitalized patients. Hence, the present invention is particularly useful for stimulating the immune system and health in these subjects and for treating and/or preventing immune system related diseases.

It was further recognized that the immune system can be suitably stimulated with a diversity of oligosaccharides of limited chain length (i.e. DP of 2, 3, 4 and/or 5). The present invention also provides a nutritional composition with a particular content of small chain oligosaccharides.

In a further aspect the present finding that sheep milk oligosaccharides stimulate the immune system enables the formulation of nutritional compositions, which can be advantageously administered to subjects with an impaired and/or underdeveloped immune system. The present composition advantageously contains immune-stimulatory sheep milk oligosaccharides and is further improved by inclusion of long chain polyunsaturated fatty acids (LC PUFA), optionally combined with nucleotides and/or reinforced with additional oligosaccharides. The combination of ingredients has a significant immune-stimulatory and immune-balancing effect, making it particularly desirable to apply e.g. in nutritional products.

The LC PUFA in combination with the sheep milk oligosaccharides is more effective and synergistically stimulates the maturation of the intestinal epithelial barrier, and/or complementary improves the cytokine profiles in patients fed with such mixture. In particular, administration of the present sheep milk oligosaccharides combined with omega 3 fatty acids such as eicosapentaenoic acid (EPA) and docosahexaenoic acid (DHA) results in a decrease of prostaglandin E2 metabolites (PGE2) production. PGE2 modulates the intensity and duration of the immune response. The present combination of oligosaccharides and LC PUFA gives an improved immune response. In a further preferred embodiment, the present composition additionally contains nucleotides, which in addition to the above, stimulate leukocytes.

It is particularly preferred that the present sheep milk oligosaccharides contain a mixture of different oligosaccharides. The present inventors believe that the diversity of oligosaccharides is an important contributor to the immune stimulatory effect. However, sheep milk oligosaccharides are relatively expensive ingredients, and in a preferred embodiment, both quantity and diversity of the oligosaccharides is increased by addition of oligosaccharides which may be chemically synthesized and/or isolated from plant material, preferably galactooligosaccharides.

In a further aspect the present invention also provides a method for isolating oligosaccharides with an immune-stimulatory action, said method including an ultrafiltration with a membrane with a cut-off between 1 and 30 kDa.

DETAILED DESCRIPTION OF PREFERRED EMBODIMENTS

The present invention provides for a use of sheep milk oligosaccharides for the manufacture of a composition for stimulating the immune system and/or for the treatment and/or prevention of immune related disorders. In a further embodiment the present invention provides a method for stimulating the immune system and/or for the treatment and/or prevention of immune related disorders, said method comprising administering sheep milk oligosaccharides.

In a further aspect the present invention provides a nutritional composition comprising i) a protein source selected from the group consisting of soy protein, pea protein and cow's milk protein; ii) long chain polyunsaturated fatty acids and iii) sheep milk oligosaccharides.

In still a further aspect the present invention provides a nutritional composition comprising i) a protein source selected from the group consisting of soy protein, pea protein and cow's milk protein; ii) long chain polyunsaturated fatty acids and iii) oligosaccharides comprising at least one oligosaccharides selected from the group consisting of 3-sialyl-lactose and 6-sialyl-lactose, and wherein at least 75 wt. % of the total oligosaccharides have a degree of polymerisation of 2, 3, 4 or 5.

In a further embodiment the present invention concerns the use of one of the above-mentioned nutritional compositions, for the manufacture of a medicament for the stimulation of the immune system and/or for the treatment and/or prevention of immune related disorders. In a further embodiment the present invention provides a method for stimulating the immune system and/or for the treatment and/or prevention of immune related disorders, said method comprising administering one of the abovementioned nutritional compositions.

In still a further aspect, the present invention provides a process for the manufacture of a nutritional composition comprising animal milk oligosaccharides, comprising the steps of:

a. subjecting sheep milk or a sheep milk fraction to an ultrafiltration step, wherein the ultrafiltration membrane has a cut-off between 1 and 30 kDa.
b. using the permeate for manufacturing of a nutritional composition, comprising soy protein, pea protein or cow's milk protein.

Subjects

The present invention relates to a composition suitable for stimulating and/or supporting the immune system. This composition is particularly advantageous for subject with an impaired immune system such infants, elderly, sick and/or hospitalized patients. Infants with the age up to about 4 years can advantageously use the present composition. The present composition and uses thereof are particularly suitable for infants with the age up to about 2 years, as the oligosaccharides, optionally combined with LC-PUFA and nucleotides can be modified to closely resemble human breast milk.

Sheep Milk Oligosaccharide

"Sheep milk oligosaccharide(s)" as used in the present invention is/are oligosaccharide(s) isolated from sheep milk. The oligosaccharides typically comprise 2-50 monosaccharide units, preferably 2-10 monosaccharide units. The oligosaccharide fraction can suitably be isolated using the method as described by Lara-Villoslada et al Clin Nutrition in press; available online 10 Jan. 2006. The sheep oligosaccharide is indigestible by the upper gastrointestinal tract of humans and preferably can act as a prebiotic component in the lower intestinal tract. Galactose, glucose and lactose are digestible.

The sheep oligosaccharides applied in the present composition and method are preferably relatively pure, and have a reduced content of other sheep milk components, particularly a low sheep milk protein content. The present composition preferably has: i) a weight ratio cow's milk protein/sheep milk protein above 1, preferably above 2, even more preferably above 5. The weight ratio sheep milk protein: sheep milk oligosaccharide is preferably below 2, more preferably below 1, most preferably below 0.5.

The present sheep milk oligosaccharide is preferably a mixture of different oligosaccharides, more preferably a mixture of at least 3 different oligosaccharides, even more preferably a mixture of at least 5 different oligosaccharides, most preferably a mixture of at least 6 different oligosaccharides. The diversity of different oligosaccharides is considered to be a main contributor to the immune-stimulatory effect. The present composition containing sheep milk oligosaccharides preferably comprises at least three oligosaccharide selected from the group consisting of N-acetyl-glucosyl-lactose, galactosyl-lactose, N-acetylneuraminyl-lactose, 3-sialyl-lactose and 6-sialyl-lactose.

The sheep milk oligosaccharides with a relatively low molecular weight are believed to be most effective. Hence the present composition preferably contains at least 50 wt. % oligosaccharides with a degree of polymerization of 2 to 6, hence 2, 3, 4, 5 and/or 6, based on total weight of oligosaccharides, more preferably at least 75 wt. %, most preferably at least 80 wt. %. Preferably the present composition contains at least 10 wt. % oligosaccharides, based on total weight of oligosaccharides, selected from the group consisting of 3-sialyl-lactose and 6-sialyl-lactose, more preferably at least 75 wt. %, most preferably at least 80 wt. %.

The finding that sheep oligosaccharides can suitably be used also resulted in the insight that mixtures of short chain oligosaccharides are particularly suitable for stimulating the immune system, particularly in combination with LC PUFA. Hence, in one aspect the present invention provides a composition with oligosaccharides, wherein the oligosaccharides comprise at least one oligosaccharide selected from the group consisting of 3-sialyl-lactose and 6-sialyl-lactose, and wherein at least 75 wt. % of the total oligosaccharides have a degree of polymerisation of 2, 3, 4, 5 or 6. This composition can also be suitably used in the present method for stimulating the immune system and/or treatment and/or prevention of immune system related disorders.

Immune System Related Disorder

It has now been found that the administration of sheep milk oligosaccharides stimulates the immune system. The term stimulating the immune system may also be indicated as supporting the immune system, balancing the immune system or similar terminology. Consequently, the present invention provides a method for the treatment and/or prevention of an immune system related disorder, said method comprising administering to a mammal, preferably a human, a composition comprising a therapeutically effective amount of sheep milk oligosaccharides.

The immune system related disorders that can advantageously be treated and/or prevented are autoimmune disorders, hereditary or conditional induced immunodeficiency and allergy. Autoimmune disorders which can suitably be treated include insuline resistant diabetes, IDDM (insulin dependent diabetes mellitus), rheumatoid arthritis, multiple sclerosis, psoriasis, scleroderma, Crohn's disease, IBD (inflammatory bowel disease), neuropathy, preferably insulin resistant diabetes (type 2 diabetes).

Conditions of hereditary or conditional induced immunodeficiency which can be suitably treated and/or prevented include immunosenescence, autism, malnutrition caused by chronic diseases, such as cancer, COPD (chronic obstructive pulmonary disease), AIDS (acquired immunodeficiency syndrome), arthritis, diabetes, anorexia, cachexia, dysphagea, kidney failure, radiation, patients suffering from chronic ulcerations and stress in more detail stress after social stress, infections of the respiratory tract, chronic infection or cigarette smoke, air pollution, radiation, chemotherapy.

The immune system related disorders which can be most advantageously treated and/or prevented with the present method are allergy, eczema and/or asthma.

Additional Oligosaccharide

As a diversity of oligosaccharides contributes to the immune-stimulatory effect of the present composition, the present composition preferably comprises additional oligosaccharides, which are not isolated from sheep milk. The additional oligosaccharides are preferably indigestible in the upper intestinal tract of humans.

These additional oligosaccharides preferably have a degree of polymerisation (DP) below 100, preferably below 40, even more preferably below 20, more preferably below 10, most preferably below 5. The DP of these oligosaccharides is at least 2. The additional oligosaccharides are also indigestible in the upper gastrointestinal tract of the human. Preferably the additional oligosaccharide is selected from the group consisting of fructooligosacchararides, galactooligosaccharides (including transgalactooligo-saccharides), fructopolysaccharides (including inulin), fucosylated oligosaccharides, and galacturonic acid based oligosaccharides (i.e. oligosaccharides comprising at least 50% galacturonic acid based on total saccharide units).

The total amount of oligosaccharide administered per day is preferably between 10 mg and 100 g, preferably between 100 mg and 50 g, even more preferably between 500 mg and 20 g.

Polyunsaturated Fatty Acids

The present oligosaccharides are preferably combined with long chain polyunsaturated fatty acids (LC PUFA). The LC PUFA's reinforce the immune stimulatory effect of the present oligosaccharides by modulating the eicosanoid synthesis and/or decreasing the production of prostaglandin E2 metabolites (PGE2). The present composition also preferably aims to provide nutrition and therefore also preferably includes saturated fats and monounsaturated fat. The LC PUFA's are preferably provided in the form of triglycerides and/or phospholipids.

The content of LC-PUFA with 20 and 22 carbon atoms in the present composition preferably does not exceed 20 wt. % of the total fat content, preferably does not exceed 15 wt. %, even more preferably does not exceed 5 wt. %. Preferably the present composition comprises at least 0.1 wt. % LC-PUFA with 20 and 22 carbon atoms of the total fat content, preferably at least 0.25 wt, more preferably at least 0.5 wt. %, even more preferably at least 0.75 wt. %.

Eicosapentaenoic acid (EPA, n-3), docosahexaenoic acid (DHA, n-3), arachidonic acid (ARA, n-6) and/or n-3 docosapentaenoic acid (DPA) can be advantageously included in the present composition, preferably EPA and DHA. The EPA content preferably does not exceed 15 wt. % of the total fat, more preferably does not exceed 1 wt. %, but is preferably at least 0.05 wt %, more preferably at least 0.1 wt. % of the total fat. The DHA content preferably does not exceed 15 wt. %, more preferably does not exceed 1 wt. %, but is at least 0.1 wt % of the total fat. The present composition preferably comprises at least 0.1 wt. % ARA based on total fat, even more preferably at least 0.25 wt. %, most preferably at least 0.5 wt. %. The ARA content preferably does not exceed 5 wt. %, more preferably does not exceed 1 wt. % of the total fat. In the ARA containing enteral composition, EPA and DHA are advantageously added to balance the action of ARA, e.g. reduce the potential proinflammatory action of ARA metabolites. Excess metabolites from ARA may cause inflammation. Hence, the present composition preferably comprises ARA, EPA and DHA, wherein the weight ratio ARA/DHA preferably is above 0.25, preferably above 0.5, even more preferably above 1. The ratio is preferably below 25. The weight ratio ARA/EPA is preferably between 1 and 100, more preferably between 5 and 20.

The present composition preferably comprises between 5 and 75 wt. % polyunsaturated fatty acids (PUFA) based on total fat, preferably between 10 and 50 wt. %.

If the present composition is used as an infant formula (e.g. a method for feeding an infant, said method comprising administering the present composition to an infant), the content of LC-PUFA, particularly the LC-PUFA with 20 and 22 carbon atoms, preferably does not exceed 3 wt. % of the total fat content as it is desirable to mimic human milk as closely as possible. For the same reason, the omega-3 LC-PUFA content preferably does not exceed 1 wt. % of the total fat content, the omega-6 LC-PUFA content preferably does not exceed 2 wt. % of the total fat content, the ARA (omega-6) content is preferably below 1 wt. % of the total fat content and/or the weight ratio EPA/DHA is preferably 1 or lower, more preferably below 0.5.

The LC-PUFA with 20 and 22 carbon atoms may be provided as free fatty acids, in triglyceride form, in phospholipid form, or as a mixture of one or more of the above. The present composition preferably comprises at least one of ARA and DHA in phospholipid form.

The present nutritional composition preferably also provides omega-9 (n-9) fatty acid (preferably oleic acid, 18:1), to provide sufficient nutrition. Preferably the present composition provides at least 15 wt. % n-9 fatty acid based on the weight of the total fatty acids, more preferably at least 25 wt %. The content of n-9 fatty acids is preferably below 80 wt. %.

Nucleotides

The present composition preferably contains a nucleotide component selected from the group consisting of nucleic acid, nucleic acid derivatives, nucleotides, nucleoside polyphosphates, polynucleotides, nucleosides, ribose, desoxyribose, and dinucleosidpolyphosphates ($Np_xN$). The nucleotide component further stimulate the immune system, acting synergistically with the present oligosaccharides.

Nucleic acids are typically heterocyclic pyrimidine bases cytosine, thymine, uridine and derivatives, like pseudouridine, dihyderouridine, ribothymidine, 4-thiouridine, 3-methylcytidine, N-acetylcytidine, lysidine as well as purine bases adenine and guanosine and derivatives, like 1-methyladenosine, N6-isopentenyladenosine, inosine, N7-methylguansine, N2-dimethylguanosine and wyosine. Nucleosides such as N-glycoside are pyrimidine or purine base glycoconjugates. Preferred nucleotides are phosphoesters of nucleosides, which are monomers or polymers in the form of oligo- or polynucleotides. For this application especially hydrolysates of desoxyribonucleic acid and ribonucleic acid, t-ribonucleic acid and ribosomes derived from animal milk, animal and plant tissues, yeasts, bifido- and lactobacteria and synthetic molecules are suitable raw material sources. (Biochemistry, Donald Voet and Judith G. Voet, John Wiley and Sons, Inc NY second edition chapter 28, pp 849).

Preferably, the present composition contains at least one, preferably at least two, even more preferably at least three nucleotides selected from the group consisting of cytidine monophosphate (CMP), guanosine monophosphate (GMP), adenosine monophosphate (AMP), uridine monophosphate (UMP), and inosine monophosphate (IMP).

In a further preferred embodiment the present composition contains ribose as a nucleotide component, preferably D-ribose. D(−)Ribose is a pentose sugar that can be purchased as crystalline product. Ribose is a main constituent of nucleic acids. Preferably the present composition contains between 0.01 wt. % and 50 wt. % ribose based on dry weight of the product, more preferably between 0.05 and 10-wt. %, even more preferably between 0.5 and 10 wt. %.

The present composition preferably comprises between 5 and 100 mg nucleosides and/or between 5 and 100 mg nucleotides per 100 gram dry weight of the composition, more preferably between 5 and 50 mg.

Foods

It was found that the present oligosaccharides can advantageously be applied in food, such as baby food and clinical food. The present finding is particularly suitable for use in infant nutrition, because the oligosaccharides, optionally combined with LC PUFA and nucleotides can optimally be formulated to closely mimic human breast milk. Such food preferably comprises lipid, protein and carbohydrate and is preferably administered in liquid form. The present composition preferably contains 5 to 25 en % protein; 30 to 60 en % carbohydrates; and 30 to 60 en % fat (en % is short for energy percentage and represents the relative amount each constituent contributes to the total caloric value of the preparation).

If the present composition is in liquid form with sufficiently low viscosity it can be used as baby foods and liquid clinical food which can be fed through a tube or a straw. In a preferred embodiment, the present composition has a viscosity below 600 mPas, preferably below 250 mPas, more preferably below 50 mPas, most preferably below 25 mPas at a shear rate of 100 $s^{-1}$ at 20° C. Whenever the term viscosity is used in the present document, this refers to the physical parameter which is determined according to the following method: The viscosity may be determined using a Carri-Med CSL rheometer. The used geometry is of conical shape (6 cm 2 deg acrylic cone) and the gap between plate and geometry is set on 55 μm. A linear continuous ramp shear rate is used from 0 to 150 $s^{-1}$ in 20 seconds.

Stool irregularities (e.g. hard stools, insufficient stool volume, diarrhoea) is a major problem in many babies and ill subjects that receive liquid foods. It was found that stool problems may be reduced by administering the present oligosaccharides in liquid food which have an osmolality between 50 and 500 mOsm/kg, more preferably between 100 and 400 mOsm/kg. In view of the above, it is also important that the liquid food does not have an excessive caloric density, however still provides sufficient calories to feed the subject. Hence, the liquid food preferably has a caloric density between 0.1 and 2.5 kcal/ml, even more preferably a caloric density of between 0.5 and 1.5 kcal/ml. An optimal osmolality, preferably combined with an optimal caloric density stimulates the immune stimulating effects of the present oligosaccharides, optionally combined with LC PUFA. A good caloric density and osmolality ensure a good bowel health without diarrhea and other dysfunctions, enabling the oligosaccharides to act as immune stimulant.

EXAMPLES

Example 1

Immune-Stimulatory Effect of Sheep Oligosaccharides

Experimental Setup

The effect of diets comprising sheep milk oligosaccharides was tested on the delayed-type hypersensitivity (DTH) response, which is a parameter for Th1 immunological response and is determined by measuring the increase in ear swelling in an animal model after local antigen challenge.

Sheep oligosaccharides were obtained as follows:

Ewe whey powder (Lactalis, France) was dissolved to 20% dry matter in tap water. The Ewe whey solution was ultrafiltrated over a membrane with a molecular weight cut off (MWCO) of 20000 D (e.g. DSS FF-UF-GR 20 PP spiral-wound membrane) to remove the whey proteins. The ultrafiltration permeate was nanofiltrated (e.g. DSS to FF-NF-GR spiral wound membrane) to remove salts. The concentrate of the nanofiltration process, containing the oligosaccharides with a dry weight content of 35-40% was evaporated until crystallization of lactose occurred. The lactose crystals were removed by filtration. The filtrate contained the oligosaccharides (10-20% of total solids).

Diets containing 1 wt. % sheep oligosaccharides based on total weight of the diet were tested in 6 weeks old C57Bl/6 mice (Harlan Nederland BV, Horst, the Netherlands). Control diet and test diet contained the same amount of lactose.

Vaccinations of the rats were started after a period of two to four weeks of adaptation to the new housing and diets. At day 0, a blood sample was collected prior to vaccination. At day 1, the first vaccination was administered subcutaneously. After three weeks, a blood sample was collected (day 21) and a booster vaccination was given (day 22). Nine days after booster injection (day 31), basal ear thickness was measured with a Digimatic outside micrometer (Mitutoyo, Veenendaal, the Netherlands) and a delayed-type hypersensitivity (DTH) response was induced by injecting antigen solution i.c. (intracutaneous) in the mouse ear pinnae. 24 h thereafter (day 32), the DTH response was measured. For the DTH responses, mice were i.c. injected with 25 μl dialysed Influvac in both ears as a DTH challenge.

Results DTH Response Sheep Milk Oligosaccharides

The diets containing dosages of 1 wt. % sheep milk oligosaccharides induced a statistically significant increase in the DTH response (see Table 1). The observed effect is indicative for the advantageous use of sheep milk oligosaccharides in the present method and composition.

TABLE 1

| Wt. % sheep milk oligosaccharides in diet | DTK response (%) |
|---|---|
| 0 (controle) | 100 |
| 1 | 217* |

* indicates significantly different (P < 0.01) from control

Example 2

Infant Nutrition with Sheep Oligosaccharides

Aptamil HA1™ (Milupa, Germany) containing 50 mg sheep milk/100 kcal oligosaccharides prepared according to example 1. Aptamil HA1 inherently contains: galactooligosaccharides, fructooligosaccharides (Raftilin HP, Orafti), 0.35 g arachidonic acid/100 g fat and 0.20 g docosahexaenoic acid/100 g fat.

The invention claimed is:

1. A nutritional composition comprising:
   (a) protein from a source selected from the group consisting of soy protein, pea protein whey, casein, hydrolysed whey and hydrolysed casein;
   (b) oligosaccharides, wherein at least 75 wt. % of the total amount oligosaccharides in the composition comprises 3-sialyl-lactose and 6-sialyl-lactose;
   (c) an oligosaccharide selected from the group consisting of fructooligosacchararides, galactooligosaccharides, fructopolysaccharides, fucosylated oligosaccharides and galacturonic acid based oligosaccharides; and
   (d) nucleotides.

2. The nutritional composition according to claim 1, wherein at least 75 wt. % of the total oligosaccharides have a degree of polymerisation of 2, 3, 4 or 5.

3. The nutritional composition according to claim 1 further comprising a long chain polyunsaturated fatty acid.

4. An infant formula comprising the nutritional composition according to claim 1.

5. The nutritional composition according to claim 1, wherein the 3-sialyl-lactose and 6-sialyl-lactose are isolated from sheep milk.

6. The nutritional composition according to claim 5, wherein the isolation comprises subjecting sheep milk or a sheep milk fraction to ultrafiltration with an ultrafiltration membrane having a cut-off between 1 and 30 kDa.

7. A method for stimulating the immune system and/or for the treatment and/or prevention of immune related disorders in a subject, comprising administering to the subject a composition according to claim 1.

8. The method according to claim 7, wherein the subject has an impaired immune system.

9. The method according to claim 7, wherein the subject is an infant, an elderly, and/or hospitalized.

10. The method according to claim 7, wherein the immune related disorder is allergy, asthma, atopic eczema and/or allergic rhinitis.

11. A process for the manufacture of a nutritional composition, comprising, combining:
   (a) protein from a source selected from the group consisting of soy protein, pea protein whey, casein, hydrolysed whey and hydrolysed casein;
   (b) oligosaccharides, wherein at least 75 wt. % of the total amount oligosaccharides in the composition comprises 3-sialyl-lactose and 6-sialyl-lactose; and
   (c) an oligosaccharide selected from the group consisting of fructooligosacchararides, galactooligosaccharides, fructopolysaccharides, fucosylated oligosaccharides and galacturonic acid based oligosaccharides; and (d) nucleotides.

12. The process according to claim 11, wherein the nutritional composition is infant formula.

13. The process according to claim 11, wherein the process further comprises combining a long chain polyunsaturated fatty acid.

* * * * *

UNITED STATES PATENT AND TRADEMARK OFFICE
CERTIFICATE OF CORRECTION

PATENT NO.         : 8,754,064 B2
APPLICATION NO.    : 12/294768
DATED              : June 17, 2014
INVENTOR(S)        : M'Rabet et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 969 days.

Signed and Sealed this
Fourth Day of August, 2015

Michelle K. Lee
*Director of the United States Patent and Trademark Office*